United States Patent
Fon et al.

(10) Patent No.: US 10,168,292 B2
(45) Date of Patent: Jan. 1, 2019

(54) NANOSCALE CALORIMETER ON CHIP AND RELATED METHODS AND DEVICES

(71) Applicant: California Institute of Technology, Pasadena, CA (US)

(72) Inventors: Chung Wah Fon, LaCanada, CA (US); Michael L. Roukes, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 110 days.

(21) Appl. No.: 13/843,217

(22) Filed: Mar. 15, 2013

(65) Prior Publication Data

US 2013/0288386 A1  Oct. 31, 2013

Related U.S. Application Data

(60) Provisional application No. 61/614,103, filed on Mar. 22, 2012.

(51) Int. Cl.
- *G01K 17/00* (2006.01)
- *G01N 25/48* (2006.01)
- *B01L 3/00* (2006.01)

(52) U.S. Cl.
CPC ............ *G01N 25/48* (2013.01); *B01L 3/5027* (2013.01); *B01L 3/5085* (2013.01); *G01K 17/006* (2013.01); *C12Q 2527/101* (2013.01)

(58) Field of Classification Search
CPC .............. B82Y 35/00; G01N 33/5032; G01N 33/54373; G01N 25/00; G01N 25/20; B01L 3/5027; G01K 17/006

See application file for complete search history.

(56) References Cited

U.S. PATENT DOCUMENTS 7,762,719 B2  7/2010 Fon et al.
7,966,898 B2  6/2011 Roukes et al.
(Continued)

FOREIGN PATENT DOCUMENTS

WO   WO 2006/073426   7/2006

OTHER PUBLICATIONS

Young Shik Shin, Keunchang Cho, Sun Hee Lim, Seok Chung, Sung-Jin Park, Chanil Chung, Dong-Chul Han, and Jun Keun Chang, "PDMS-based micro PCR chip with Parylene coating", J. Micromech. Microeng, 13(2003) 768-774.*
(Continued)

*Primary Examiner* — Erik B Crawford
(74) *Attorney, Agent, or Firm* — The Marbury Law Group, PLLC

(57) ABSTRACT

An article comprising: an array of calorimeter devices, wherein the device comprises: at least one fluidic enclosure disposed on a microfluidic chip, wherein the fluidic enclosure is substantially gas impermeable; at least one first chamber and at least one second chamber, wherein the first chamber and the second chamber are disposed within and enclosed by the fluidic enclosure, wherein the first chamber and the second chamber are not vacuum encapsulated; at least two microfluidic channels connected to the first chamber and at least two microfluidic channels connected to the second chamber; and at least one thermal sensor disposed between the chip and the first and second chambers, wherein the thermal sensor is adapted to measure a temperature differential between the first and second chambers. Examples include DSC and TSA devices. Biological binding and melting experiments can be done with high sensitivity.

29 Claims, 6 Drawing Sheets

(56) References Cited

U.S. PATENT DOCUMENTS

| | | | |
|---|---|---|---|
| 2003/0059807 A1* | 3/2003 | Roach | C12Q 1/6825 435/6.11 |
| 2003/0186453 A1* | 10/2003 | Bell et al. | 436/147 |
| 2003/0235924 A1* | 12/2003 | Adams | B01L 3/502715 436/172 |
| 2004/0022677 A1* | 2/2004 | Wohlstadter et al. | 422/52 |
| 2007/0286254 A1* | 12/2007 | Fon | G01K 17/006 374/31 |
| 2008/0080586 A1* | 4/2008 | Huetter | G01K 7/028 374/31 |
| 2009/0317859 A1* | 12/2009 | Daniels | C12Q 1/04 435/34 |

OTHER PUBLICATIONS

Frank H Niesen, Helena Berglund, Masoud Vedadi, "The use of differential scanning fluorimetry to detect ligand interactions that promote protein stability", Nature Protocol, 2(9) 2007, 2212-2221.*

Baier V, et al. "Highly sensitive thermopile heat power sensor for micro-fluid calorimetry of biochemical processes", Sens Actuators A Phys. 2005;123-124:354-359.

Chancellor EB, et al. "Heat conduction calorimeter for massively parallel high-throughput measurements with picoliter sample volumes", Appl Phys Lett. 2004; 85: pp. 2408-2410.

Johannessen, EA, et al. "Micromachined nanocalorimetric sensor for ultra-low-volume cell-based assays", Anal Chem. 2002; 74: pp. 2190-2197.

Lama RF, et. al.,. Excess thermodynamic properties of aqueous alcohol solutions. Chem Eng Data. 1965; 10: pp. 216-219.

Lee, W., "High-sensitivity microfluidic calorimeters for biological and chemical applications", Natl Acad Sci USA, 2009, vol. 106, No. 36, pp. 15225-15230.

Lerchner J, et al. "Nano-calorimetry of small-sized biological samples". Therm Acta. 2008;477:48-53.

Lerchner J, et al. "Recent developments in integrated circuit calorimetry". J Therm Anal Calorim. 1999;57: pp. 241-251.

Ng, JM, et al. "Components for integrated poly(dimethylsiloxane) microfluidic systems", Electrophoresis. 2002; 23, pp. 3461-3478.

Noh, HS, et al. "Parylene micromolding, a rapid and low-cost fabrication method for parylene microchannel" Sens Actuators B Chem. 2004;102, pp. 78-85.

Recht MI, et al. "Enthalpy array analysis of enzymatic and binding reactions", Anal Biochem. 2008;377, pp. 33-39.

Thorsen, T, et al., "Dynamic pattern formation in a vesicle-generating microfluidic device" Phys Rev Lett. 2001 ;86, pp. 4163-4166.

Torres, FE, et al. "Enthalpy arrays", Proc Natl Acad Sci USA. 2004;101, pp. 9517-9522.

Verhaegen K, et al., "A high-throughput silicon microphysiometer". Sens Actuators A Phys. 2000; 82, pp. 186-190.

Wang L, et al. "A MEMS thermal biosensor for metabolic monitoring applications", J Microelectromech Sys. 2008;17, pp. 318-327.

Webster JR, et al., "Monolithic capillary electrophoresis device with integrated fluorescence detector", Anal Chem. 2001; 73, pp. 1622-1626.

Wiseman T, et al., "Rapid measurement of binding constants and heats of binding using a new titration calorimeter". Anal Biochem. 1989;179, pp. 131-137.

Xie J, et al., "An electrochemical pumping system for on-chip gradient generation". Anal Chem. 2004; 76, pp. 3756-3763.

Xie J, et al., "Surface micromachined electrostatically actuated micro peristaltic pump", Lab Chip. 2004; 4 pp. 495-501.

Xu J, et al. "A microfabricated nanocalorimeter: Design, characterization, and chemical calibration", Anal Chem. 2008; 80: pp. 2728-2733.

Yamashita O, et al. "Bismuth telluride compounds with high thermoelectric figures of merit". J Appl Phys. 2003; 93: pp. 368-374.

Zhang Y et al., "Calorimetric biosensors with integrated microfluidic channels", Biosens Bioelectron. 2004;19:pp. 1733-1743.

Invitation to Pay Additional Fees with Partial Search Report received in connection with international application No. PCT/US2013/032621; dated Mar. 14, 2014.

Esfandyarpour et. al., "An Integrated Differential Nanoclaimeter with On-Chip Microfluidic Multiplexing for High Throughput Genomics and Proteomics"; 14$^{th}$ International Conference on Miniaturized Systems for Chemistry and Life Sciences; MicroTAS (2010); pp. 1349-1351.

Wang et al., "A MEMS Nanocalorimeter for Biomolecular Characterization", Proceedings of the 1$^{st}$ IEEE International Conference on Nano/Micro Engineered and Molecular Systems; pp. 349-352 (2006).

Wang et al., "Demonstration of MEMS-based differential scanning calorimetry for determining thermodynamic properties of biomolecules", Sensors and Actuators B:Chemical; vol. 134; pp. 953-958 (2008).

* cited by examiner

NANOSCALE CALORIMETER ON CHIP AND RELATED METHODS AND DEVICES

CROSS-REFERENCE TO RELATED APPLICATIONS

This application claims priority under 35 U.S.C. § 119(e) to U.S. Provisional Application No. 61/614,103, filed Mar. 22, 2012, which is incorporated herein by reference in its entirety for all purposes.

BACKGROUND

Calorimetry is increasingly an important method not just for synthetic materials and industrial processes, but also for biological and pharmaceutical applications. For example, isothermal titration calorimetry (ITC), including both differential scanning calorimetry (DSC) and thermal shift assays (TSA) (also, known as Differential Scanning Fluorimetry (DSF)), conventionally refers to a family of techniques for probing various thermal-related properties of, for example, chemical reactions, biomolecules, or biological species. ITC is used in a variety of scientific fields, including but not limited to proteomics, genetics, molecular biology, and drug discovery. DSC can measure, for example, heat capacity at different temperatures. TSA can measure, for example, an interaction between a fluorescent probe and a sample.

Current ITC technologies, however, can be prohibitively costly in terms of speed, sensitivity, and required amounts of sample. Major challenges to devising high-performance microcalorimeter devices include, among other things, maintaining heat retention and providing isolation from environmental disturbances. Further, as reaction volume decreases, heat production and therefore signal reduces proportionally, thereby adversely affecting miniaturization efforts for DSC and TSA technologies.

To date, employment of DSC and TSA at the microscale has been extremely limited due to the shortcomings of present instruments in throughput and operation costs. Furthermore, conventional DSC instruments do not offer the ability to also perform TSA measurements, and current TSA instruments do not offer the ability to also perform DSC measurements. Hence, a need exists for better devices and methods.

SUMMARY

Embodiments described herein include articles and devices, as well as methods of making and methods of using devices.

One embodiment provides, for example, an article comprising: an array of calorimeter devices, wherein the device comprises: at least one fluidic enclosure disposed on a microfluidic chip, wherein the fluidic enclosure is substantially gas impermeable; at least one first chamber and at least one second chamber, wherein the first chamber and the second chamber are disposed within and enclosed by the fluidic enclosure, wherein the first chamber and the second chamber are not vacuum encapsulated; at least two microfluidic channels connected to the first chamber and at least two microfluidic channels connected to the second chamber; at least one thermal sensor disposed between the chip and the first and second chambers, wherein the thermal sensor is adapted to measure a temperature differential between the first and second chambers; and at least one heater in thermal communication with at least one chamber.

In one embodiment, the fluidic enclosure is a chemically inert polymer. In one embodiment, the polymer is at least one epoxy-based material, at least one poly(p-xylylene) polymer, or a combination thereof.

In one embodiment, the first chamber and the second chamber are suspended chambers.

In one embodiment, the fluidic enclosure is optically transparent.

In one embodiment, the first chamber and the second chamber are adapted to contain at most a nanoliter scale volume.

In one embodiment, the channel walls comprise at least one epoxy-based material, at least one poly(p-xylylene) polymer, or a combination thereof. In one embodiment, the channels have walls that are less than about 1 micrometer thick.

In one embodiment, the thermal sensor is a thermopile. In one embodiment, the thermopile comprises gold or an alloy comprising one or more of gold-nickel, constantan-gold, poly-silicon, bismuth telluride, or some combination thereof. In one embodiment, the thermal sensor comprises a plurality of thermocouples connected in series. In one embodiment, the thermal sensor provides about 1 µK to about 100 µK temperature resolution.

In one embodiment, the chip comprises at least one membrane to support the fluidic enclosure and the thermal sensor. In one embodiment, the membrane comprises silicon nitride. In one embodiment, the membrane supports the floor of the first chamber and second chamber and an antireflective layer. In one embodiment, the membrane is less than about 1 µm thick.

In one embodiment, the article further comprises silicone microfluidics directly connected to at least one channel connected to the first chamber and at least one channel connected to the second chamber, wherein the silicone microfluidics comprise at least one pump, at least one valve, and at least one mixer. In one embodiment, the pump is a peristaltic pump. In one embodiment, the mixer is a ring mixer, a chaotic mixer, or a butterfly-shape-channel mixer.

In one embodiment, the at least one heater comprises a first heater in thermal communication with the first chamber and a second heater, different from the first heater, in thermal communication with the second chamber. In one embodiment, the heater is an electrical heater. In one embodiment, the heater is a gold-resistive heater. In one embodiment, the heater is adapted to provide a heat pulse. In one embodiment, the heater acts as a thermometer.

In one embodiment, the array comprises about 8 to about 400 devices.

In one embodiment, the device further comprises at least one photodiode connected to the first chamber and at least one photodiode connected to the second chamber. In one embodiment, the photodiode is located off-chip.

In one embodiment, the device is adapted to measure a heat capacity or a fluorescence signal.

In one embodiment, the microfluidic chip comprises a silicon wafer to provide anchoring and suspended portions to the microfluidic chip.

In one embodiment, the microfluidic chip is about 100 mm to about 300 mm in diameter.

Another embodiment provides for an article comprising an array of calorimeter devices, wherein the devices are adapted to measure the thermal response or fluorescent response of a sample, wherein the response is associated with melting or unfolding of at least one component of the sample, stability of the sample, or strength of a binding or interaction involving at least one component of the sample.

In one embodiment, the device comprises a fluidic enclosure disposed on a microfluidic chip, wherein the fluidic enclosure is substantially gas impermeable.

In one embodiment, the device comprises a first chamber and a second chamber, wherein the first chamber and the second chamber are disposed within and enclosed by the fluidic enclosure, wherein the first chamber and the second chamber are not vacuum encapsulated.

In one embodiment, the device comprises at least one microfluidic channel adapted for inlet of a sample into the first chamber, at least one microfluidic channel adapted for outlet of the sample from the first chamber, at least one microfluidic channel adapted for inlet a sample into the second chamber, at least one microfluidic channel adapted for outlet of the sample from the second chamber.

In one embodiment, the device comprises a thermal sensor located adjacent to a first chamber and a second chamber, wherein the sensor is adapted to measure the temperature differential between the first and second chambers.

In one embodiment, the device is adapted to contain a nL scale sample comprising the biochemical species.

In one embodiment, the device comprises a photodiode connected to the first and chamber and a photodiode connected to the second chamber.

In one embodiment, the photodiodes are located off-chip.

In one embodiment, the device further comprises silicone microfluidics directly connected to the channels, wherein the silicone microfluidics comprise at least one pump, at least one valve, and at least one mixer.

In one embodiment, the at least one heater comprises a first heater located adjacent to the first chamber and a second heater located adjacent to the second chamber.

In one embodiment, for example, an article comprises: an array of calorimeter devices, wherein the device comprises: at least one fluidic enclosure disposed on a microfluidic chip, wherein the fluidic enclosure is substantially gas impermeable; at least one chamber, wherein the chamber is disposed within and enclosed by the fluidic enclosure, wherein the chamber is not vacuum encapsulated, and wherein the chamber is transparent and has a high transmission efficiency; at least two microfluidic channels connected to the chamber; at least one heater in thermal communication with the chamber; and a camera positioned to detect fluorescence from the chamber.

In another embodiment, a method of screening a sample is provided comprising: (a) providing an array of calorimeter devices according to embodiments described herein; (b) loading a screening sample into the first chamber of at least one device; (c) loading a reference sample into the second chamber of at least one device; (d) thereafter sweeping the temperature of the samples in the chambers; and (e) measuring a temperature response of the samples in the first chamber and the second chamber, wherein the temperature response is measured with the thermal sensor; wherein the samples used in the first and second chambers of each device can be the same or different from the samples used in the first and second chambers of the other devices.

In one embodiment, one or both of the screening sample and the reference sample comprise one or more biochemical species, therapeutic agents, antimicrobial agents, bioactive substances, small molecules, large molecules, proteins, nucleic acids, macromolecular complexes, analytes, ligands, adjuvants, buffering agents, detergents, lipids, chemical stabilizers, denaturants, or a combination thereof.

In one embodiment, the screening sample contains a biochemical species and a ligand.

In one embodiment, the reference sample does not contain the ligand.

In one embodiment, the ligand is a small molecule.

In one embodiment, the loading is through the microfluidic channels.

In one embodiment, the method further comprises moving the sample through the microfluidic channels with at least one silicone peristaltic pump connected to at least one of the channels.

In one embodiment, the sweeping is over a temperature range of about 25° C. to about 80° C.

In one embodiment, the sweeping is performed with heat pulses.

In one embodiment, the sweeping is achieved by a computer controlled system.

In one embodiment, the temperature sweep is performed in at most about 60 seconds.

In one embodiment, the temperature response is heat capacity.

In one embodiment, the method further comprises mixing the biochemical species with the ligand before loading the sample into the chamber.

In one embodiment, the mixing is performed by a ring mixer, a chaotic mixer or a butterfly-shape-channel mixer.

In one embodiment, the first and second chambers can independently hold a nL scale sample volume or less.

In one embodiment, the method uses 1 ng or less of biochemical species per chamber.

In one embodiment, the method further comprises characterizing the melting or unfolding at least one component of the screening sample, stability of at least one component of the screening sample, or strength of binding or interactions involving at least one component of the screening sample, wherein the characterizing is based on the temperature response of the samples in the first and second chambers.

In one embodiment, the array comprises about 8 to about 400 devices.

In one embodiment, the method screens for target affinity.

In one embodiment, the method screens for conditions for protein stability.

Another embodiment provides for a method of screening a sample comprising: (a) providing an array of calorimeter devices, wherein a device comprises: at least one fluidic enclosure disposed on a microfluidic chip, wherein the fluidic enclosure is substantially gas impermeable, and wherein the fluidic enclosure is optically transparent; at least a first chamber and a second chamber, wherein the chambers are disposed within and enclosed by the fluidic enclosure, and wherein the first chamber and the second chamber are not vacuum encapsulated; at least two microfluidic channels connected to the first chamber and at least two microfluidic channels connected to the second chamber; at least one heater in thermal communication with at least one chamber; and at least one photodiode connected to the first chamber and at least one photodiode connected to the second chamber, or at least one camera positioned to detect fluorescence from the chambers; (b) loading a first screening sample into the first chamber of at least one device, wherein the first screening sample comprises at least one fluorescent probe; optionally, (c) loading a second screening sample into the second chamber of at least one device, wherein the second screening sample comprises at least one fluorescent probe; (d) thereafter sweeping the temperature of the samples; and (e) measuring a fluorescence response of the samples in the first chamber and the second chamber; wherein the samples used in the first and second chambers of each device can be the same or different from each other or from the samples used in the first and second chambers of the other devices.

In one embodiment, the fluorescent probe is a fluorescent dye.

In one embodiment, one or both of the screening sample and the reference sample comprise one or more biochemical species, therapeutic agents, antimicrobial agents, bioactive substances, small molecules, large molecules, proteins, nucleic acids, macromolecular complexes, analytes, ligands, adjuvants, buffering agents, detergent, lipids, chemical stabilizers, denaturants, or a combination thereof.

In one embodiment, the screening sample contains the biochemical species and the ligand.

In one embodiment, the first screening sample is different from the second screening sample.

In one embodiment, the ligand is a small molecule.

In one embodiment, the loading is through the microfluidic channels.

In one embodiment, the method further comprises moving the sample through the microfluidic channels with at least one silicone peristaltic pump connected to at least one of the channels.

In one embodiment, the sweeping is over a temperature range of about 25° C. to about 80° C.

In one embodiment, the sweeping is performed with heat pulses.

In one embodiment, the sweeping is achieved by a computer controlled system.

In one embodiment, the temperature sweep is performed in at most about 60 seconds.

In one embodiment, the fluorescence response is measured with the at least one photodiode.

In one embodiment, the method further comprises mixing the biochemical species with the ligand before loading the sample into the chamber.

In one embodiment, the mixing is passive microfluidic mixing.

In one embodiment, the mixing is performed by a ring mixer, a chaotic mixer or a butterfly-shape-channel mixer.

In one embodiment, the first and second chambers can independently hold a nL scale sample volume or less.

In one embodiment, the method uses 1 ng or less of biochemical species per chamber.

In one embodiment, the method, further comprises characterizing the melting or unfolding at least one component of the screening sample, stability of at least one component of the screening sample, or strength of binding or interactions involving at least one component of the screening sample, wherein the characterizing is based on the temperature response of the samples in the first and second chambers.

In one embodiment, the array comprises about 8 to about 400 devices.

In one embodiment, the method screens for target affinity.

In one embodiment, the method screens for conditions for protein stability.

In one embodiment, an article is provided comprising: a microarray of calorimeter devices, wherein a device comprises: (a) at least one fluidic enclosure disposed on a microfluidic chip, wherein the fluidic enclosure comprises Parylene or SU-8, and wherein the fluidic enclosure is optically transparent; (b) at least a first chamber and a second chamber, wherein the chambers are disposed within the fluidic enclosure, wherein the chambers are not vacuum encapsulated, wherein the chambers are suspended and enclosed, and wherein the chambers are adapted to contain at most a nanoliter scale volume; (c) at least two microfluidic channels connected to the first chamber and at least two microfluidic channels connected to the second chamber; (d) a thermal sensor disposed between the chip and the first and second chambers, wherein the sensor is adapted to measure a temperature differential between the first and second chambers; (e) at least one membrane disposed between the fluidic enclosure and the microfluidic chip, wherein the membrane comprises at least one wall of the chambers, and wherein the membrane comprises Parylene, silicon nitride, or some combination thereof; (f) at least a first microheater located adjacent to the first chamber and a second microheater located adjacent to the second chamber; (g) silicone microfluidics directly connected at least one channel connected to the first chamber and at least one channel connected to the second chamber, wherein the silicone microfluidics comprise at least one pump, at least one valve, and at least one mixer; and (h) optionally, at least one photodiode connected to the first chamber and at least one photodiode connected to the second chamber; wherein the array comprises about 8 to about 400 devices.

In one embodiment, a method of screening a sample is provided comprising: (a) providing an array according to embodiments described herein; (b) loading a screening sample into a first chamber of at least one device; (c) loading a reference sample into the second chamber of at least one device; (d) thereafter sweeping the temperature of the samples; and (e) measuring a temperature response of the samples in the first chamber and the second chamber, wherein the temperature response is measured with the thermal sensor; wherein the samples used in the first and second chambers of each device can be the same or different from the samples used in the first and second chambers of the other devices.

In one embodiment, a method of screening a sample is provided comprising: (a) providing an array according to embodiments described herein; (b) loading a first screening sample into the first chamber of at least one device, wherein the first screening sample comprises at least one fluorescent probe; (c) loading a second screening sample into the second chamber of at least one device, wherein the second screening sample comprises at least one fluorescent probe; (d) thereafter sweeping the temperature of the samples; and (e) measuring a fluorescence response of the first screening sample and the second screening sample; wherein the first screening sample and the second screening sample can be the same or different from each other or from the samples used in the first and second chambers of the other devices.

In one embodiment, a method of screening a sample is provided comprising: (a) providing an array according to embodiments described herein; (b) loading a screening sample into the first chamber of at least one device, wherein the screening sample loaded into the first chamber of at least one device comprises at least one fluorescent probe; (c) loading a reference sample into the second chamber of at least one device, wherein the reference sample loaded into the second chamber of at least one device comprises at least one fluorescent probe; (d) thereafter sweeping the temperature of the samples; (e) measuring a fluorescence response of the samples in the first chamber and the second chamber of at least one device; and (f) measuring a temperature response of the samples in the first chamber and the second chamber of at least one device, wherein the temperature response is measured with the thermal sensor; wherein the samples used in the first and second chambers of each device can be the same or different from the samples used in the first and second chambers of the other devices.

At least one advantage for at least one embodiment includes a high speed of response. At least one additional advantage for at least one embodiment includes high throughput. At least one additional advantage for at least one embodiment includes sensitivity. At least one additional advantage for at least one embodiment includes a small chamber volume. At least one additional advantage for at least one embodiment is temperature stability of the array over time. At least one additional advantage for at least one embodiment is sample uniformity during measurement.

DETAILED DESCRIPTION

Figure 1A:
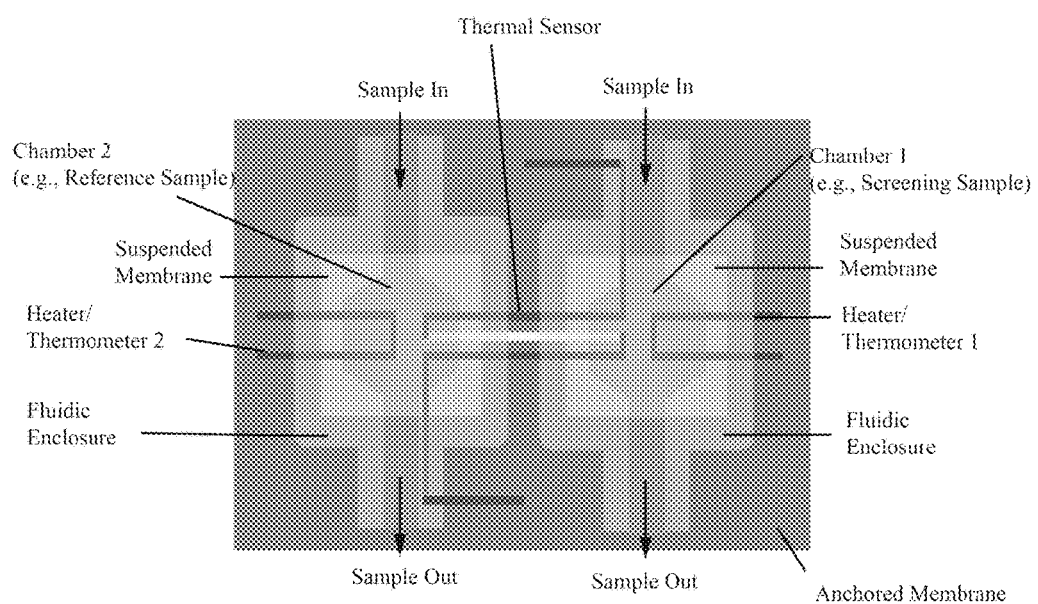
FIG. 1A shows one embodiment, a top view schematic of a two chamber calorimeter device.

Array of Calorimeter Devices, Differential Scanning Calorimetry (DSC) Devices or Thermal Shift Assay (TSA) Devices The present disclosure relates to a Microelectromechanical system (MEMS)-based or nanoelectromechanical system (NEMS)-based array of microfluidic coupled calorimeter devices, such as DSC devices or TSA devices. MEMS and NEMS include devices with features having a size of 1 micron to 100 microns and 1 nanometer to less than 1 micron, respectively, in at least one dimension, and preferably in two or three dimensions. Among other things, the high sensitivity and performance attained distinguish the present arrays from conventional and commercial calorimeters. For example, some embodiments of the present disclosure can provide high speed of response (~100 ms), high throughput, and/or high sensitivity (presently nW-scale power sensitivity, corresponding to only about ~100 μK rise in chamber temperature). Some embodiments can have 100 pW power resolution. Some embodiments described herein can combine a small reaction chamber volume down to the nanoliter (nL) or picoliter (pL) scale, high thermal isolation, and an enclosed chamber that provides complete enclosure from air, thereby circumventing fluidic sample loss via evaporation. Furthermore, some embodiments have negligible electrical power dissipation, high resolution in temperature and power, and/or the capability of precise fluid injection/mixing. Especially noteworthy is that these calorimeter arrays can be batch produced by conventional MEMS surface micromachining.

In some embodiments, the array has from about 4 calorimeter devices to about 400 calorimeter devices. In some embodiments, the devices are arranged in rows and columns. In some embodiments, the array is disposed on a microfluidic chip. The microfluidic chip can be made from any suitable material, for example silicon. A chip can be any size suitable for holding a device, for example between about 5 mm to about 3 cm. The chip can be any size suitable for holding an array, for example between about 100 mm to about 300 mm in diameter.

In some embodiments, the array can be reusable. In some embodiments, the array can be disposable.

Device Chambers

In some embodiments, a calorimeter device can have at least one chamber adapted to hold a sample. In some embodiments, the chamber is adapted to hold a liquid sample. In some embodiments the device has two chambers, as illustrated, for example, in FIGS. 1A-B, and 2. In some embodiments, the device can have at least a first chamber and a second chamber which are different from each other. In some embodiments, the first chamber and the second chamber can have the same or substantially the same volume (e.g., one value within 25% of the other value). For example, each chamber can have a volume of up to about 900 nL, up to about 500 nL, up to about 250 nL, up to about 100 nL, up to about 50 nL, up to about 10 nL, or up to about 1 nL. In some embodiments, each chamber can have a volume of about 3 nL to about 10 nL. In some embodiments, each chamber can have a pL scale volume. For example, each chamber can have a volume of up to about 900 pL, or up to about 500 pL.

In some embodiments, the first chamber and the second chamber have identical configurations or mirror image configurations.

The shape of the chamber is not limited as long as functionality is achieved. For example, in some embodiments the chamber can be square or rectangular shaped. In some embodiments the chamber can have a round shape. In some embodiments, the chamber can have an irregular shape. In some embodiments, the chamber can have at least one tapered edge. In some embodiments, the tapered edge can ensure that the chamber can be substantially filled with a sample.

In some embodiments, the chamber height can be about 5 μm or less, about 10 μm or less, about 15 μm or less, about 20 μm or less, about 50 μm or less, or about 100 μm or less. In some embodiments, the chamber height can be about 100 μm or more. In some embodiments, the height of the chambers is between about 15 μm to about 20 μm.

In some embodiments, the chamber can have a diameter of about 200 μm to about 400 μm.

Figure 1B:
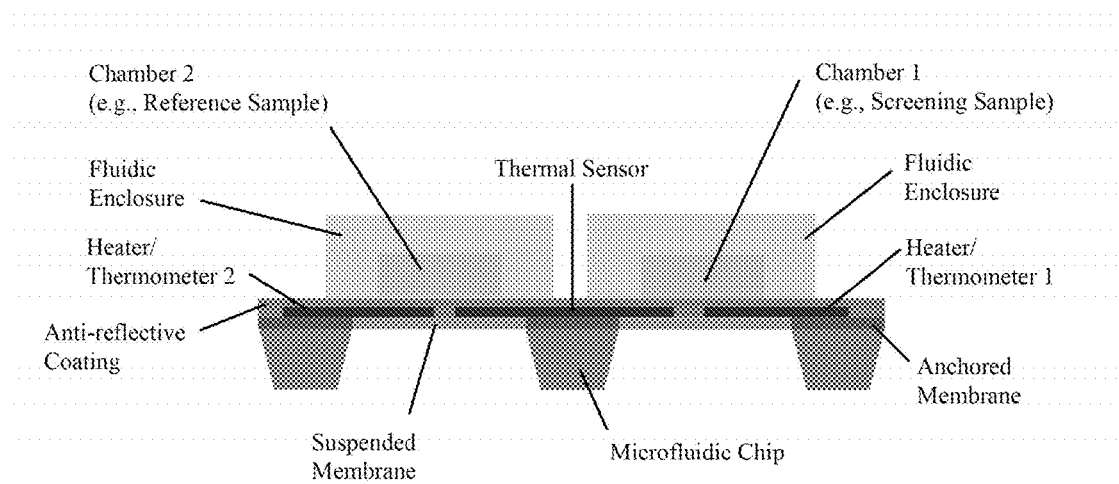
FIG. 1B shows one embodiment, a cross-section schematic of a two chamber calorimeter device.

In some embodiments, the at least first chamber and second chamber can be arranged side by side. In some embodiments, the chamber can be suspended. Without being bound by theory, it is believed that suspending the chamber thermally isolates the chamber from the environment. Suspending can be done by any suitable means, for example by forming the chamber on a suspended fluidic enclosure or by removing a portion of the chip supporting the chamber, such as by reactive ion etching. In some embodiments, the chamber can be suspended by wet etching of silicon with potassium hydroxide. In some embodiments, the chamber can be suspended by wet etching of silicon dioxide with hydrofluoric acid. FIG. 1B illustrates an example of suspended chambers.

In some embodiments, chamber can be disposed within at least one fluidic enclosure, wherein the fluidic enclosure can be disposed on a microfluidic chip. In some embodiments, the first chamber and the second chamber can be disposed within at least one fluidic enclosure. In some embodiments, the fluidic enclosure layer can be comprised of a polymer membrane. In some embodiments, the fluidic enclosure can be comprised of a chemically inert polymer. In some embodiments, the fluidic enclosure can be substantially gas impermeable. In some embodiments, the fluidic enclosure can be biocompatible. In some embodiments, the fluidic enclosure can be transparent. In some embodiments, the fluidic enclosure can be optically transparent. In some embodiments, the fluidic enclosure or chamber can have a high transmission efficiency, for example for fluorescence, such as at least about 70% efficiency, at least about 80% efficiency, at least about 90% efficiency, at least about 95% efficiency, at least about 98% efficiency, or at least about 99% efficiency. In some embodiments, the fluidic enclosure or chamber allows fluorescence detection through the fluidic enclosure. In some embodiments, the fluidic enclosure or chamber has very low background fluorescence. In some embodiments the fluidic enclosure can be morphed to form the shape of the chambers. In some embodiments, the fluidic enclosure can be comprised of a permanent resist. The fluidic enclosure can be made of any suitable material, for example an epoxy-based material (e.g., SU-8), poly(p-xylylene) polymers (e.g., Parylene), or a combination thereof.

In some embodiments, the fluidic enclosure can be patterned onto the microfluidic chip. In some embodiments, the fluidic enclosure can be formed by polymerization from crosslinking of one or more suitable materials. In some embodiments, the fluidic enclosure can be deposited with vapor-phase deposition. In some embodiments, the fluidic enclosure can be deposited with 3D printing, and can be comprised of, for example, polymers commonly used in 3D printing.

In some embodiments, the chambers can be disposed between at least one membrane, such that the membrane defines at least one floor of each chamber, and at least one fluidic enclosure, such that the fluidic enclosure defines the remaining walls of each chamber. FIG. 1B illustrates one example of this embodiment. In some embodiments, the membrane can be, for example, less than about 1 µm thick, or less than about 500 nm thick. The membrane can comprise any suitable material, for example silicon nitride, silicon, polymers, or a combination thereof. In some embodiments, the membrane can be a dielectric or polymer membrane. In some embodiments, the membrane is positioned between the fluidic enclosure and the chip. In some embodiments, the membrane is coated with an anti-reflective coating, for example WiDE-15B. In some embodiments, the coated membrane forms at least one wall of the chambers.

In some embodiments, the chambers are enclosed, for example by the fluidic enclosure. Without being bound by theory, it is believed that enclosing the chamber prevents vaporization, and helps avoid temperature and concentration drift or fluctuation. In some embodiments, the enclosure can allow substantially no gas permeability. In some embodiments, the enclosure can be optically transparent. In some embodiments, the enclosure can be structurally strong enough to prevent the chamber from collapsing.

In some embodiments, the chambers can have high, but not absolute, thermal isolation from the environment. In some embodiments, chambers are not vacuum encapsulated. In some embodiments, thermal isolation is achieved by disposing the chambers on a suspended membrane. Without being bound by theory, it is believed that vacuum encapsulation can increase measurement time and limit the bandwidth for observation. It is also believed that vacuum encapsulation can cause, at least in some embodiments, an adverse shift in heat capacity, and can slow down a reaction without improving the quality of the data.

Device Channels

Figure 2:
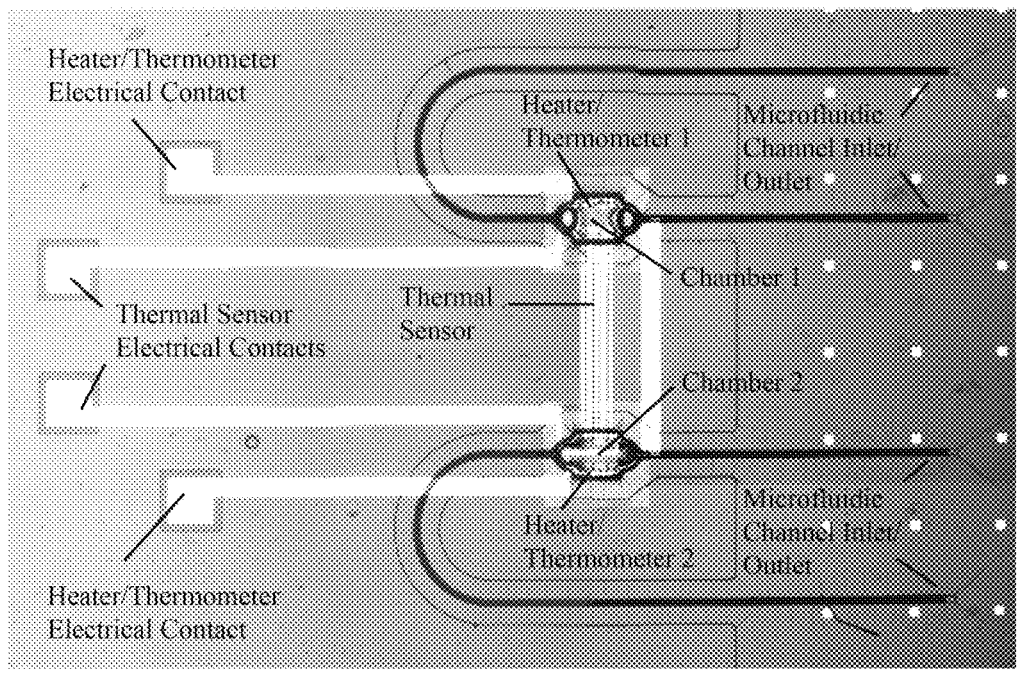
FIG. 2 shows one embodiment from the working examples, a two chamber DSC device with electrical contacts.
Figure 3A:
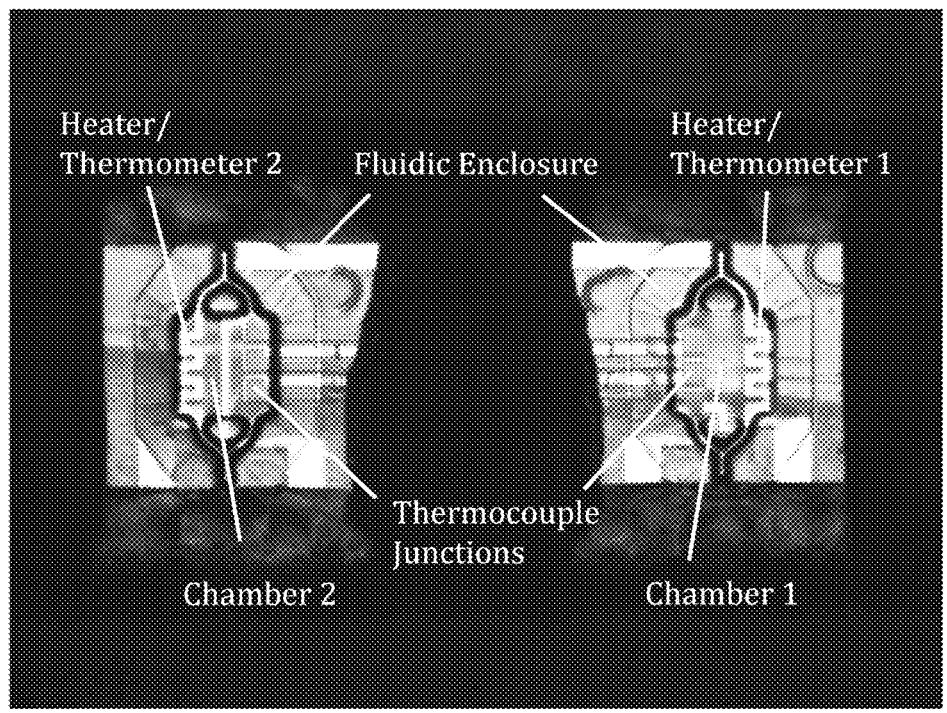
FIG. 3A shows one embodiment from the working examples, a two chamber DSC device.
Figure 3B:
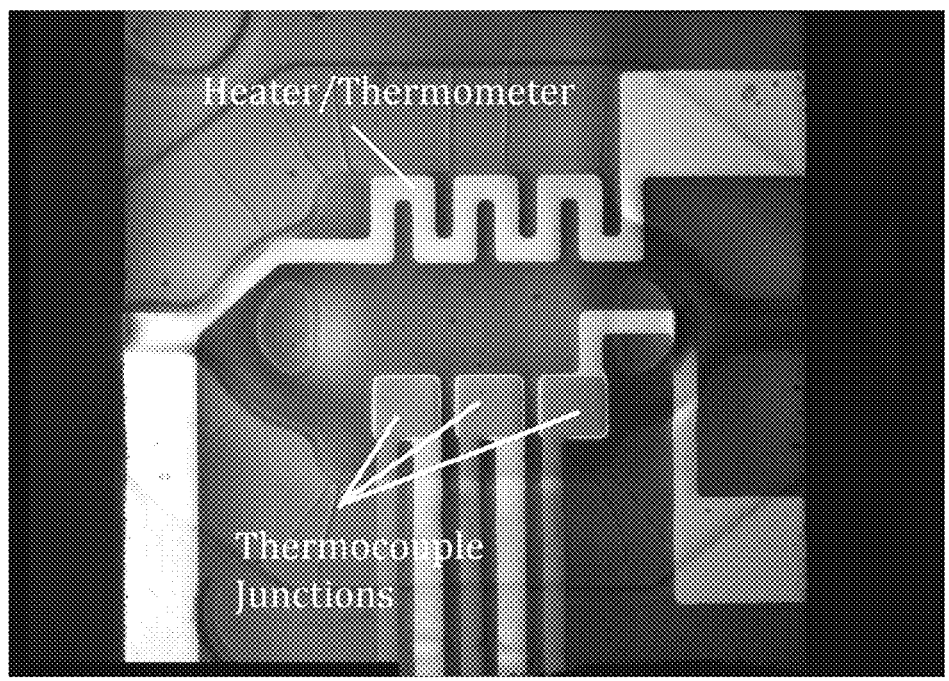
FIG. 3B shows one embodiment, an enlarged in view of a DSC chamber in FIG. 3A that shows thermocoupled junctions and a microheater.

In some embodiments, the device has at least two channels connected to at least one chamber. In some embodiments, the device has at least two channels connected to at least a first chamber and at least two channels connected to a second chamber. FIGS. 1A and 2 represent an example of a device in which two channels are connected to the first chamber and two channels are connected to the second chamber. FIG. 3 represents an example of a chamber with four connected channels. In some embodiments, at least one channel can be used for inlet of a sample into a chamber, and at least one channel can be used for outlet a sample from a chamber. The length of the channels is not limited, and can be for example between about 0.1 mm to about 10 mm long. The width of the channels is not limited, and can be for example about 10 µm to about 100 µm wide, such as about 30 µm wide. The walls of the channel can be about 1 µm to about 150 µm thick. In some embodiments, the channel walls can be about 1 µm thick. The height of the channels can be about 5 µm or less, about 10 µm or less, about 15 µm or less, about 20 µm or less, about 50 µm or less, or about 100 µm or less. In some embodiments, the chamber height can be about 100 µm or more. In some embodiments, the height of the channels is between about 15 µm to about 20 µm.

In some embodiments, the path of the channels is not limited. In some embodiments, the cross-section shape of the channels is not limited. For example, the channel cross-section can be round, square, rectangular, or irregular shaped.

In some embodiments, the channels are disposed between at least one membrane, such that the membrane defines at least one wall of the channels, and a fluidic enclosure, such that the fluidic enclosure defines the remaining walls of the channels. An example of one such embodiment is illustrated in FIG. 1A-B. In some embodiments, the membrane can be, for example, less than about 1 µm thick, or less than about 500 nm thick. The membrane can comprise any suitable material, for example silicon nitride, silicon, polymers, or a combination thereof. In some embodiments, the membrane can be a dielectric or polymer membrane. In some embodiments, the membrane is positioned between the fluidic enclosure and the chip. In some embodiments, the membrane is coated with an anti-reflective coating, for example WiDE-15B. In some embodiments, the coated membrane forms at least one wall of the channels.

In some embodiments, the fluidic enclosure layer can be comprised of a polymer membrane. In some embodiments, the fluidic enclosure can be comprised of a chemically inert polymer. In some embodiments, the fluidic enclosure can be substantially gas impermeable. In some embodiments, the fluidic enclosure is biocompatible. In some embodiments, the fluidic enclosure can be morphed to form the shape of the channels. In some embodiments, the fluidic enclosure can be comprised of a permanent resist. The fluidic enclosure can be made of any suitable material, for example an epoxy-based material (e.g., SU-8), poly(p-xylylene) polymers (e.g., Parylene), or a combination thereof.

In some embodiments, the channels can be formed by any known methods, for example by forming a hollow structure using a double exposure technique. In some embodiments, anti-reflective coating can be used to aid in the formation of a hollow structure.

In some embodiments, a plurality of inlet channels connect to the chamber. In some embodiments, at least one channel can be used for inlet of at least one component of a sample into the chamber and at least one channel can be used for inlet of at least one other component into the chamber. In some embodiments, at least one channel can be used for inlet a reference sample, or a portion thereof, into the chamber.

In some embodiments, a single channel is connected to the chamber for inlet of a sample into the chamber. In some embodiments, multiple channels can merge into a single inlet channel, and the single channel can connect to the chamber.

In some embodiments, at least one outlet channel is connected to the chamber for removal of the sample from the chamber.

Thermal Sensor

In some embodiments, a thermal sensor can be located between the fluidic enclosure and the chip, wherein the sensor is adjacent to the first chamber and the second chamber. FIGS. 1A-B illustrate an example a device with a thermal sensor. A thermal sensor can be, for example, coated on, embedded, or otherwise included in the membrane. In some embodiments, the sensor can be configured to measure the temperature differential between the two chambers. In some embodiments, the thermal sensor can monitor the chamber temperatures in real time.

In some embodiments, the thermal sensor is a thermoelectric sensor. In some embodiments, the thermal sensor is a thermopile. In some embodiments, the thermal sensor is a resistive sensor.

In some embodiments, the thermal sensors can have at least one contact pad that can extend outside the device for external electrical connection, as shown for example in FIG. 2. In some embodiments, the device can be connected to, for example, a power supply, an amplifier, or any suitable data acquisition instrument.

Without being bound by theory, it is believed that the metallic electrical connection impacts thermal isolation of the device, and increased amounts and thicknesses of metal lead can lead to excessive heat loss. In some embodiments, therefore, the thickness of the metal used can be less than about 100 nm thick.

A thermopile can include a plurality of elongated segments of similar or dissimilar materials, where adjacent segments of materials are joined together at opposite ends, thereby forming thermocouple junctions. An example of thermocouple junctions can be seen, for example, in FIGS. 4A-B. In some embodiments, the thermopile can have between about three to about 30 adjacent segments. Thermocouple junctions can be located between the microfluidic chip and each chamber (e.g., under each chamber). In some embodiments, at least about 3 to about 15 junctions are located under each chamber. Junctions can be, for example, aligned to the central axis of each chamber.

In some embodiments, at least about 3 to about 15 thermocouples are stacked and connected in series. In some embodiments, the thermal sensor is made with thermoelectric materials with high Seebeck coefficients. For example, in some embodiments the sensor is made with a material having a Seebeck coefficient of about 5 µV/K to about 500 µV/K. Materials with high Seebeck coefficients include, but are not limited to gold, doped polysilicons, and bismuth tellurium.

The material for the thermopile can include a variety of similar or dissimilar pairs of metals, e.g., antimony-bismuth (Sb—Bi), or other pairs of materials providing high thermoelectric efficiency, such as n-type and p-type bismuth telluride, n-type and p-type antimony telluride, Nickel, Gold, or some combination thereof. The material can be, for example, an alloy such as gold-nickel, constantan-gold, poly-silicon, bismuth-telluride, or some combination thereof.

In some embodiments, the thermal sensor provides a temperature resolution of about 1 µK to about 100 µK, for example about 100 µK.

In some embodiments, the thermal sensor has an impedance of less than about 100 ohm.

Heaters

In some embodiments, the device can further comprise at least one microheater. In some embodiments, the device can further include a first set of microheaters and a second set of microheaters which are aligned underneath or adjacent to the first chamber and the second chamber, respectively. FIGS. 1A-B and 4A-B illustrate or represent examples of a device with at least one microheater. The microheaters can be, for example, coated on, embedded, or otherwise included in the membrane. In some embodiments, the microheaters are insulated from the thermal sensors. In some embodiments, the microheaters are provided in a different membrane layer than the thermal sensors.

In some embodiments, the microheaters can have at least one contact pad that can extend outside the device for external electrical connection, as shown for example in FIG. 2. In some embodiments, the device can be connected to, for example, a power supply, an amplifier, or any suitable instrumentation.

In some embodiments the microheaters can be patterned to provide uniform heating of the chambers. For example, the microheaters can be disposed in a meandering pattern between the chambers and the chip. One example of a microheater with a meandering pattern can be seen in FIG. 3A-B. In some embodiments, the microheaters are adapted to heat the chambers with one or more heat pulses. In some embodiments, the microheater can be comprised of a metal, alloy, or semiconductor. In some embodiments, the microheater can be gold with a thin chrome layer underneath as an adhesion layer. In some embodiments, the heater is an electrical heater, for example a gold-resistive heater.

In some embodiments, the microheater can act as a thermometer. In some embodiments, the microheater can be used as a thermometer to save space. In some embodiments, the microheater can be used as a thermometer to reduce electrical connections.

In some embodiments, the thermometer can be calibrated against a known source, such as a platinum resistance thermometer, for accurate temperature sensing. In some embodiments, the thermometer is in thermal contact and equilibrium with the known source during calibration. In some embodiments, the thermal equilibrium can be attended by putting the device in a temperature controlled environment, for example an over.

Silicone/PDMS Microfluidics

Figure 4:
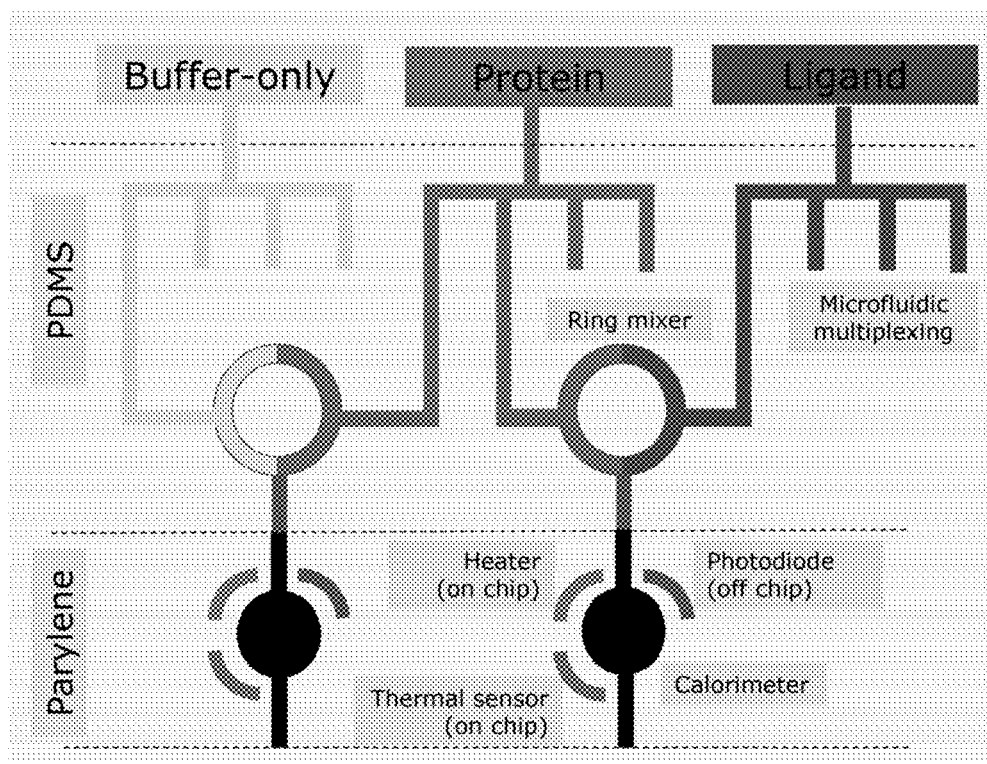
FIG. 4 shows a schematic of a two chamber microfluidic DSC or TSA device for testing protein-ligand binding according to one embodiment.

In some embodiments, the device can be interfaced with a soft polymer, such as silicone, such as polydimethylsiloxane (PDMS) microfluidics. For use herein, polydimethylsiloxane is an example of a silicone. The materials can be crosslinked or uncrosslinked. FIG. 4 illustrates an example of PDMS microfluidics. Microfluidic systems used in embodiments of the present invention have been described before, for example in US 2011/0216804. In some embodiments, the PDMS microfluidics comprise at least one valve. In some embodiments, the PDMS microfluidics comprise at least one pump. In some embodiments, the PDMS microfluidics comprise at least one mixer. In some embodiments, the PDMS microfluidics can comprise a control layer. In some embodiments, the control layer can comprise valves and pumps. In some embodiments, the pumps are peristaltic pumps. In some embodiments, the valves are pneumatic valves.

In some embodiments, the control layer can be connected to and used to control the flow of a sample in a flow layer. In some embodiments, the flow layer can be connected to the device channels. In some embodiments, the flow layer is connected to the device channels through a via, for example an SU-8 via.

In some embodiments, connection of the device with PDMS microfluidics allows for automated control without pipetting.

In some embodiments, PDMS microfluidics can comprise at least one PCR device. In some embodiments, PDMS microfluidics can comprise at least one protein crystallization chip.

In some embodiments, PDMS microfluidics allows transfer of materials with minimal sample loss.

PDMS is but one example.

Mixer

In some embodiments, the device comprises a mixer. The mixer can be present in either the fluidic enclosure layer or the silicon/PDMS microfluidic layer. In some embodiments, at least two reagents are separately introduced into a chamber, and the reagents mix via passive diffusion.

In some embodiments, the reagents are combined and flow through a mixer before entering the chamber. In some embodiments, the mixer can substantially mix 10 nL to 500 nL volumes in about 10 ms to about 50 ms.

In some embodiments, the mixer is a passive mixer, for example a chaotic mixer or a butterfly-shape channel mixer. In some embodiments, the mixer is a ring mixer. In a chaotic mixer, at least a portion of the channel walls can have ridges to generate turbulence as the sample flows through the channel. In a butterfly-shape channel mixer, the channel can have sharp corners or turns.

In some embodiments, the mixing schemes are defined by a SU-8 permanent photoresist. In some embodiments, mixing schemes are included in the mask design of the microfluidic channels.

In some embodiments, the mixer is present in the fluidic enclosure channels. In some embodiments, the mixer is present in PDMS microfluidics layer. In some embodiments, the mixer is thermally isolated. In some embodiments, the mixer can be present on-chip. In some embodiments, the mixer can be present off-chip.

Optical Detection

In some embodiments, the device further comprises at least one photodiode. In some embodiments, at least one photodiode is connected to the first chamber and at least one photodiode is connected to the second chamber. Other arrangements known in the art can be used. In some embodiments, the photodiode can be located off-chip. In some embodiments, the photodiode can be located on-chip. In some embodiments, the photodiode can detect fluorescence from the device chamber, which can comprise an optically transparent fluidic enclosure.

In some embodiments, at least one camera can be used for optical, such as fluorescent, detection. In some embodiments, the camera can be positioned to detect fluorescence from at least one device. In some embodiments, the camera can be positioned to detect fluorescence from all devices. In some embodiments, the camera is connected to the array.

Method of Screening a Sample

In some embodiments, the array disclosed herein can be used for screening a sample. For example the array can be used to screen for binding affinity, protein stability, or condition optimization. In some embodiments, a method of screening a sample can comprise (a) providing an array of calorimeter devices, as disclosed herein, (b) loading a screening sample into a first chamber of a device, (c) loading a reference sample into a second chamber of the device, (d) sweeping the temperature of at least one device, and (e) measuring a differential response of the screening sample and reference sample to the temperature sweep.

In some embodiments, a method of screening a sample can comprise (a) providing an array of calorimeter devices, as disclosed herein, (b) loading a screening sample into at least one chamber of a device, (c) sweeping the temperature of at least one device, and (d) measuring, and (d) measuring a fluorescence response of the sample to the temperature sweep.

In some embodiments, an array can be used for both DSC and TSA. In some embodiments, DSC and TSA can be performed simultaneously with a single array. In some embodiments, DSC and TSA can be performed simultaneously within a single device. In some embodiments, at least one of the of the devices in an array is used as a DSC, and at least one of the devices in an array is used as a TSA. In some embodiments, all devices in an array are used as DSCs. In some embodiments, all devices in an array are used as TSAs.

Screening and Reference Samples

The screening sample can comprise any screenable components. For example, the screening sample can comprise one or more biochemical species, therapeutic agents, antimicrobial agents, bioactive substances, small molecules, large molecules, protein, nucleic acids, macromolecular complexes, analytes, ligands, adjuvants, buffering agents, detergents, lipids, chemical stabilizers, denaturants, or a combination thereof.

In some embodiments, the screening sample can comprise a protein and a ligand, as illustrated for example in FIG. 4. The ligand can be any compound or molecule capable of binding with the protein, for example a large or small molecule. The protein can be any protein, for example hemagglutinin or a variant thereof. In some embodiments, less than about 1 ng, less than about 5 ng, less than about 10 ng, or less than about 50 ng of protein is loaded into a chamber. In some embodiments, the sample concentration can be about 50 µM to about 1 mM. In some embodiments, the total amount of protein used for the entire screening can be less than about 10 µg protein. In some embodiments, less than about 10 µg protein can be used to run about 5000 to about 20,000 operations, for example about 10,000 operations.

In some embodiments, more than about 8, more than about 20, more than about 50, more than about 100, more than about 200, more than about 400, or more than about 1,000 screening samples can be arrayed simultaneously.

In some embodiments, the screening sample can comprise chemical stabilizers or denaturants, for example urea, guanidinium hydrochloride, glycerol, detergents, or some combination thereof.

In some embodiments, screening samples can include a range of pH values.

The reference sample can be the same or different from the screening sample. In some embodiments, the reference sample can comprise substantially the same components as the screening sample, except without the component being screened. In some embodiments, the reference sample can be identical to the screening sample in terms of constituents and concentrations, except that the reference sample does not comprise the component being screened. In some embodiments, the reference sample can comprise components with known interactions or effects.

In some embodiments, one or both of the screening sample and the reference sample can comprise a fluorescent probe. In some embodiments, the fluorescent probe is a fluorescent dye, for example ThermLuor, ProteoStat, or Sypro Orange. In some embodiments, the fluorescent probe can interact with the screening or reference sample. In some embodiments, the fluorescent probe in the screening sample is the same as the fluorescent probe in the reference sample.

Loading/Unloading the Screening and Reference Samples

In some embodiments, the samples are loaded into the chambers through microfluidic channels. In some embodiments, less than about 900 nL, less than about 500 nL, less than about 250 nL, less than about 100 nL, less than about 50 nL, less than about 10 nL, less than about 1 nL can be loaded into each chamber.

In some embodiments, the screening sample and reference sample are independently mixed before being loaded into the first and second chamber, respectively. An example of one embodiment is illustrated by FIG. 4, wherein prior to loading the samples into their respective chambers, protein and ligand are mixed together to form a screening sample and protein and buffer are mixed together to form a reference sample. In some embodiments, the screening sample and reference sample are loaded into their respective chambers by being pushed through the microfluidic channels by microfluidic pumps. In some embodiments, the screening sample and reference sample are loaded into their respective chambers simultaneously. In some embodiments, screening samples are loaded into both the first and second chamber. In some embodiments, screening samples comprising fluorescent probes are loaded into the chambers. In some embodiments, one screening sample is loaded into the first chamber of the device, and a second screening sample is loaded into the second chamber of the device. In some embodiments, the screening and/or reference samples loaded into the chambers of a device can be the same or different from the screening and/or references samples loaded into the chambers of other devices in the array.

In some embodiments, the screening and reference samples can be unloaded or discharged from the chambers. Unloading or discharge can be through any suitable means, for example by pushing a solvent, such as water, alcohol, or buffer, through the microfluidic channels and chambers. In some embodiments, the device can be rinsed with isopropyl alcohol and water, for example distilled water.

Temperature Sweeping and Differential Response Measurement

In some embodiments, the temperature of the samples in the first and second chambers is incrementally increased from a range of about 20° C. to about 99° C., or about 25° C. to about 80° C., or 25° C. to about 75° C. In some embodiments, the temperature can be changed in about 0.01° C. to about 0.1° C. steps. In some embodiments, each temperature step can last less than about 0.5 seconds. In some embodiments, the temperature sweep can be completed in less than about 1 minute, less than about 15 minutes, less than about 20 minutes, or less than about 30 minutes.

The temperature sweep can be performed, for example, by releasing heat pulses from the at least one microheater. In some embodiments, each heat pulse can last about 0.1 seconds to about 10 seconds. In some embodiments, the temperature sweep can be initiated electronically, for example with a computer interface. In some embodiments, the temperature sweep of the first chamber and the second chamber can be performed simultaneously.

In some embodiments, the temperature sweep can be performed using conventional means. For example, a heat power (P2) can be applied to the second chamber to sweep the chamber across a temperature range. The temperature sweep can be continuous, such that the temperature in the chamber is not at a steady state. The temperature of the second chamber (T2) can be recorded. Simultaneously, a heat power (P1) can be applied to the first chamber so that the temperature difference (dT) between the first chamber and the second chamber is about zero. Because the first chamber, for example, can contain the screening sample, P1 can be larger than P2 due to the extra heat capacity. P2 can form the reference of the measurement, while P1−P2 provides the heat capacity of the component being measured. Measurement can be recorded, for example, every 0.1° C.

In conventional measurement, T1 and T2 are not at a steady state because the thermal time constant can be very long, for example about 3 to about 5 minutes. Disadvantages of the conventional measurement are that temperature spatial gradients, differences, and errors in the chamber or solution contribute to error in the measurement and limit the scanning rate. Further, rescanning is not possible because of slow cooling-heating cycles.

In some embodiments, the temperature sweep is performed using microfluidic methods. In such embodiments, the above problems are avoided because thermalization is fast, for example less than 1 second. In microfluidic methods, step-wise measurements can be performed. The heating powers have two components, $P=P_{DC}+P_{AC}$. The DC component is frequency independent and can heat the chambers to keep them at a steady temperature. To measure the heat capacity, an AC component, for example at a frequency of about 1 Hz to about 100 Hz, can be applied. The heat capacity can be determined from the differential temperature signal at the AC frequency if identical AC components are applied to both the first chamber and the second chamber. Alternatively, $P1_{AC}$ and $P2_{AC}$ can be tuned, in both amplitude and phase, to ensure zero differentials in temperatures. In such a case, heat capacity of a protein can be extracted from the difference of $P1_{AC}$ and $P2_{AC}$.

In some embodiments, the differential response between the screening sample and reference sample can be measured. In some embodiments, calorimeter devices can measure the differential heat capacity across the temperature sweep range. The heat capacity can enable characterization of one or more of a variety of factors, for example, protein melting, protein folding or unfolding, protein stability, protein intermolecular interactions, protein intramolecular interactions, or protein ligand binding.

In some embodiments, the differential response can be measured with the thermal sensors. In some embodiments, the differential response can be analyzed via software data analysis.

In some embodiments, the calorimeter devices can measure a fluorescent signal. The optical fluorescent signal can be measured, for example, with a photodiode or camera. The signal can be measured, for example, through the walls of an optically transparent chamber. In some embodiments, the fluorescent signal from each chamber is independently measured.

In some embodiments, a fluorescent probe can bind, for example, with the hydrophobic surfaces of a protein that are exposed during protein melting or unfolding. The differential fluorescent signal can enable characterization of one or more of a variety of factors, for example, protein melting, protein folding or unfolding, protein stability, protein intermolecular interactions, protein intramolecular interactions, or protein-ligand binding.

Embodiments

The below embodiments represent non-limiting examples of the present invention or elements thereof.

In some embodiments, an article comprises an array of differential scanning calorimeter devices or thermal shift assay devices, wherein a device comprises (a) at least one fluidic enclosure disposed on a microfluidic chip, wherein the fluidic enclosure is substantially gas impermeable; (b) at least a first chamber and a second chamber, wherein the first chamber and the second chamber are disposed within the fluidic enclosure, and wherein the first chamber and the second chamber are not vacuum encapsulated; (c) at least two microfluidic channels connected to the first chamber and at least two microfluidic channels connected to the second chamber; (d) a thermoelectric sensor disposed between the chip and the first and second chambers, wherein the sensor is adapted to measure a temperature differential between the first and second chambers; (e) at least one heater in thermal communication with at least one chamber; and, optionally (f) a photodiode or camera.

In some embodiments, a method of screening a sample comprises (a) providing an array as disclosed herein; (b) loading a screening sample into the first chamber of at least one device; (c) loading a reference sample into the second chamber of at least one device; (d) sweeping the temperature of the samples; and (e) measuring a temperature response of the samples in the first chamber and the second chamber; wherein the samples used in the first and second chambers of each device can be the same or different from the samples used in the first and second chambers of the other devices. In some embodiments, the temperature response is heat capacity. In some embodiments, the temperature response is fluorescence.

Some embodiments can be illustrated by the present figures. For example, FIG. 1A-B shows a schematic of one embodiment of a device. The schematic illustrates a device with a first chamber and a second chamber. The device comprises a fluidic enclosure disposed on a microfluidic chip. A membrane is disposed on the microfluidic chip, and the membrane, which can be coated with an antireflective coating, comprises one wall of each of the first and second chambers. The remaining walls of the first and second chambers are comprised of the fluidic enclosure. The membrane can be either suspended or anchored, with the first and second chambers disposed on a suspended membrane. A thermal sensor can disposed on or in the membrane, and is positioned adjacent to both the first chamber and the second chamber. At first microheater and a second microheater can be disposed adjacent to the first and second chamber, respectively. The heaters can also function as thermometers. Samples can be loaded into the chambers through inlet channels, and can be removed from the chambers through outlet channels.

FIG. 2 shows an example of an embodiment in which the thermal sensor and heaters in a two-chamber device can be prepared with electrical contacts. These electrical contact can be used to connect the device to, for example, a power supply, amplifier, and/or data acquisition instrument.

FIG. 4A-B shows an example of a two-chamber device. FIG. 4A illustrates a chamber wall that can be formed with the fluidic enclosure. In the figure, the bottom of the chambers are comprised of a membrane. A thermal sensor extends from a central portion of the first chamber to a central portion of the second chamber, and is located under the chambers. The thermal sensor can be comprised of multiple metal components, which are joined together at thermocouple junctions.

Embodiments of the present invention can be created based on the following non-limiting working example.

WORKING EXAMPLE

Example 1

An array of eight devices was fabricated on a 100 mm diameter single-side polished silicon wafer. See exemplary devices in FIGS. 2 and 3A-B. A 300 nm layer of semiconductive silicon nitride (SiN) was deposited onto the wafer by low pressure vapor deposition. The SiN layer was coated with a photoresist, and three Nickel wires were formed on top of the SiN layer by electron-beam evaporation followed by photoresist dissolution. The Ni wires were 25 µm wide and 1.25 mm long. Additionally, four gold (Au) wires (3 for a thermal sensor, and one for a microheater shared by both chambers) were formed on top of the SiN layer in the same manner. The metal layers were subsequently patterned via optical lithography and wet chemical etching to form the thermopiles. Some of the Au wires were connected end to end to the Ni wires to form a thermopile, and some Au wires were used for heating and thermometry.

Squares were patterned on the backside of the wafer via optical lithography, such that for each device (two chambers), two squares were patterned. Each square was 1.2 mm wide, and the center-to-center distance between the two squares from 1.4 mm. The SiN under the patterned squares were removed via reactive ion etching (RIE). The silicon above the squares was removed during a 5 hour etch with potassium hydroxide at 85° C. and 30% concentration (mass/mass). The RIE and wet etch resulted in two suspended SiN membranes on the frontside of the wafer for each device. The width of the membrane was 450 µm.

Microfluidic chambers and channels were formed with permanent resist SU-8, which formed the side-walls and top of the channels and chambers. The SiN layer formed the bottom wall of the chambers and channels. Openings were formed at the end of the SU-8 channels for outside fluidic connection.

In forming the chambers and channels, an anti-reflective coating (WiDE-15B, Brewser Science) was spun onto the wafer and baked. Next, a 25 µm thick SU-8 film was spun on and baked. A pattern of the microfluidic sidewall was exposed by optical lithography. The energy of exposure was about 1 W/cm². Next the pattern of the top of the channel was exposed with a low dosage of about 75 mW/cm². The exposure formed a round chamber with a diameter of about 200 µm to about 400 µm, depending on the direction of measurement. The chamber volume was about 2 nl. The width of the microfluidic channels was about 30 µm. The height of the channels and the chamber was about 20 µm.

The exposed SU-8 was cured into a permanent solid by post-exposure baking at 65° C. for 30 min. After baking, the wafer was cooled to room temperature at about 10° C./hr. Finally, the unexposed SU-8 resist was developed by PGMEA solvent. The resist residing inside the channel and chamber was evacuated through the SU-8 opening at the end of the channel.

What is claimed is:
1. An article comprising: an array of calorimeter devices, wherein the calorimeter devices each comprise:

at least one fluidic enclosure disposed on a microfluidic chip, wherein the fluidic enclosure is substantially gas impermeable and consists essentially of substantially gas impermeable material;

at least one first chamber and at least one second chamber, wherein the first chamber and the second chamber are disposed within and enclosed by the fluidic enclosure, wherein the first chamber and the second chamber are not vacuum encapsulated, wherein each of the first chamber and the second chamber contain have at most a nanoliter scale volume of up to 100 nL, and wherein the first chamber and the second chamber have a chamber height of 50 microns or less;

at least two microfluidic channels connected to the first chamber and at least two microfluidic channels connected to the second chamber;

at least one thermal sensor disposed between the chip and the first and second chambers, wherein the thermal sensor is adapted to measure a temperature differential between the first and second chambers, wherein the at least one thermal sensor comprises a plurality of thermocouples connected in series, and wherein the thermal sensor provides about 1ρK to about 100 μK temperature resolution;

at least one heater in thermal communication with at least one of the first chamber or the second chamber; and at least one photodiode connected to the first chamber and at least one photodiode connected to the second chamber, and wherein the photodiode is located off-chip with respect to the microfluidic chip.

2. The article of claim 1, wherein the fluidic enclosure is a chemically inert polymer.

3. The article of claim 2, wherein the polymer is at least one epoxy-based material, at least one poly(p-xylylene) polymer, or a combination thereof.

4. The article of claim 1, wherein the first chamber and the second chamber are suspended chambers.

5. The article of claim 1, wherein the fluidic enclosure is optically transparent.

6. The article of claim 1, wherein each of the first chamber and the second chamber have at most a nanoliter scale volume of up to 10 nL.

7. The article of claim 1, wherein the microfluidic channels connected to the first chamber and the microfluidic channels connected to the second chamber comprise channel walls, and wherein the channel walls comprise at least one epoxy-based material, at least one poly(p-xylylene) polymer, or a combination thereof.

8. The article of claim 1, wherein the channels have walls that are less than about 1 micrometer thick.

9. The article of claim 1, wherein the thermal sensor is a thermopile.

10. The article of claim 9, wherein the thermopile comprises gold or an alloy comprising one or more of gold-nickel, constantan-gold, poly-silicon, bismuth telluride, or some combination thereof.

11. The article of claim 1, wherein the chip comprises at least one membrane to support the fluidic enclosure and the thermal sensor.

12. The article of claim 11, wherein the membrane is less than about 1 μm thick.

13. The article of claim 1, wherein the at least one heater comprises a first heater in thermal communication with the first chamber and a second heater, different from the first heater, in thermal communication with the second chamber.

14. The article of claim 13, wherein the heater is an electrical heater.

15. The article of claim 1, wherein the array comprises about 8 to about 400 of the calorimeter devices.

16. The article of claim 1, wherein each of the calorimeter devices measures a heat capacity or a fluorescence signal.

17. A method of screening a sample comprising:
(a) providing an array of calorimeter devices according to claim 1;
(b) loading a screening sample into the first chamber of at least one device;
(c) loading a reference sample into the second chamber of at least one device;
(d) thereafter sweeping the temperature of the samples in the chambers; and
(e) measuring a temperature response of the samples in the first chamber and the second chamber, wherein the temperature response is measured with the thermal sensor;
wherein the samples used in the first and second chambers of each device can be the same or different from the samples used in the first and second chambers of the other devices.

18. The method of claim 17, wherein one or both of the screening sample and the reference sample comprise one or more biochemical species, therapeutic agents, antimicrobial agents, bioactive substances, small molecules, large molecules, proteins, nucleic acids, macromolecular complexes, analytes, ligands, adjuvants, buffering agents, detergents, lipids, chemical stabilizers, denaturants, or a combination thereof.

19. The method of claim 17, wherein the screening sample contains a biochemical species and a ligand.

20. The method of claim 19, wherein the reference sample does not contain the ligand.

21. The method of claim 17, wherein the loading is through the microfluidic channels.

22. The method of claim 21, further comprising moving the sample through the microfluidic channels with at least one silicone peristaltic pump connected to at least one of the channels.

23. The method of claim 17, wherein the sweeping is over a temperature range of about 25° C. to about 80° C.

24. The method of claim 17, wherein the sweeping is performed with heat pulses.

25. The method of claim 17, wherein the temperature sweep is performed in at most about 60 seconds.

26. The method of claim 17, wherein the temperature response is heat capacity.

27. The method of claim 18, further comprising mixing the biochemical species with the ligand before loading the sample into the chamber.

28. The method of claim 17, further comprising characterizing the melting or unfolding at least one component of the screening sample, stability of at least one component of the screening sample, or strength of binding or interactions involving at least one component of the screening sample, wherein the characterizing is based on the temperature response of the samples in the first and second chambers.

29. The method of claim 17, wherein the method screens for conditions for protein stability.

* * * * *